(12) United States Patent
Kasowski

(10) Patent No.: US 8,703,853 B2
(45) Date of Patent: Apr. 22, 2014

(54) FLAME RETARDANT AND COMPOSITION CONTAINING IT

(71) Applicant: Robert Valentine Kasowski, West Chester, PA (US)

(72) Inventor: Robert Valentine Kasowski, West Chester, PA (US)

(*) Notice: Subject to any disclaimer, the term of this patent is extended or adjusted under 35 U.S.C. 154(b) by 0 days.

(21) Appl. No.: 13/986,979

(22) Filed: Jun. 20, 2013

(65) Prior Publication Data

US 2013/0341575 A1    Dec. 26, 2013

Related U.S. Application Data

(62) Division of application No. 13/261,332, filed on Jun. 21, 2012.

(51) Int. Cl.
*C08K 5/51*    (2006.01)

(52) U.S. Cl.
USPC .......................................................... 524/148

(58) Field of Classification Search
USPC .......................................................... 524/148
See application file for complete search history.

(56) References Cited

U.S. PATENT DOCUMENTS

2009/0048372 A1*    2/2009  Kasowski ..................... 524/86

* cited by examiner

*Primary Examiner* — Peter Szekely

(57) ABSTRACT

Ethyleneamine polyphosphates are good flame retardants. Use of non viscous phase enables making modified ethyleneamine polyphosphate of enhanced thermal stability and greatly reduced waste stream. Addition of fillers such as fumed silica unexpectedly improve the flame retardance. Organic phosphates improve compatibility.

17 Claims, No Drawings

FLAME RETARDANT AND COMPOSITION CONTAINING IT

FIELD OF INVENTION

This invention relates to flame retardant syrups, flame retardants and compositions containing these flame retardants (FR) as well as a method for their preparation.

BACKGROUND OF INVENTION

Ethyleneamine polyphosphates as described in U.S. Pat. No. 7,138,443 and US patent application 20090048372 are effective environmentally friendly halogen free flame retardants. However ethyleneamine polyphosphate has some deficiencies in practical use. (1) Preparation of ethyleneamine polyphosphate is inefficient. The process in U.S. Pat. No. 7,138,443 and US patent application 20090048372 has less than an 85% yield, resulting in a 15% non viscous phase or more. The non viscous phase has a high phosphorous content and many publically operated treatment facilities (POT) cannot accept such a non viscous phase leading to a costly disposal problem. (3) TGA indicates that ethyleneamine polyphosphates made according to U.S. Pat. No. 7,138,443 start to decompose at a temperature of 300° C., which will cause problems in extrusion when such temperatures are reached. (4) The efficiency of flame retardants of U.S. Pat. No. 7,138,443 would be more efficient if they decomposed at temperatures above 350 C to be closer to decomposition temperature of polymers. (5) Polymers containing ethyleneamine polyphosphates sag or drip when exposed to a flame in the UL94 test. (6) It is difficult to load more than about 25% of ethyleneamine polyphosphates into polymers such as polypropylene and a compatibilizer is needed for high loadings. (7) In US patent application 20090048372, ethyleneamine polyphosphates are claimed with stability better than 1.5% at 315° C.

The flame retardants of this invention helps to greatly reduce the problems of dripping and/or sagging of polymeric compositions containing ethyleneamine polyphosphate in a flame. Finally, a new ethyleneamine polyphosphate is invented that is at least 45° C. more stable than the standard ethyleneamine polyphosphate of U.S. Pat. No. 7,138,443 and the new process has better than 95% yield and utilizes the non viscous phase of U.S. Pat. No. 7,138,443. A compatibilizer is also defined.

SUMMARY OF INVENTION

This invention provides flame retardant compositions that provide flame retardation for a variety of applications, such as replacement of flame retardants containing halogens. The flame retardant used in many applications contain brominated or chlorinated compounds. There is a ready market for flame retardants that do not contain halogens, which this invention addresses. It is important that not only the flame retardant is halogen free but there not be severe handling problems when using mixers to insert the flame retardant into polymers. It is also important that the flame retardant be very stable and the process for making it not create significant waste stream needing expensive remediation.

This invention is a flame retardant syrup prepared by a method comprising the steps of (a) dissolving sodium polyphosphate in a dilute ethyleneamine polyphosphate solution with less than 10% concentration, (b) purifying such sodium polyphosphate solution via ion exchange resin to obtain a modified polyphosphoric acid, (c) reacting an ethyleneamine or a mixture of ethyleneamines with the modified polyphosphoric acid to form a two phase mixture, (d) collecting and separating syrup from dilute non viscous phase, with said non viscous phase saved for next iteration. Typically, the non viscous phase is substituted for the dilute ethyleneamine polyphosphate solution step (a). Typically, the flame retardant syrup of claim 1 has pH between 1 and 7. The utilization of non viscous phase has great benefit and was unexpected.

This invention is also a filled flame retardant syrup which contains fillers selected from the group of melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates. The flame retardant composition is obtained by drying the flame retardant syrup by any method including vacuum ovens and hot nitrogen.

This invention is also a filled flame retardant composition comprising the above flame retardant composition which further contain fillers selected from the group of organic phosphates; melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates. The preferred organic phosphate is BDP or RDP.

This invention is also a flame retardant containing composition comprising: a) 30 to 99.75 percent by weight of a polymer; and b) 0.25 to 70 percent by weight of the above flame retardant compositions.

Finally, this invention also includes a filled flame retardant containing composition comprising: a) 30 to 99.75 percent by weight of a polymer; b) 0.25 to 70 percent by weight of flame retardant compositions above and c) 0.01 to 40% of one or more compounds selected from the group of organic phosphates; melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates.

Other ingredients may be added to these compositions: For example, pigments are added for color. Mica, nano-clay, chopped glass, carbon fibers, aramids, and other ingredients can be added to alter mechanical properties. Other flame retardants both non-halogen and halogen can be added to form a flame retarded composition in order to capture synergies between different chemistries.

The addition of fumed silicas and BDP (bisphenol A bis-diphenylphosphate) directly to dehydrated ethyleneamine polyphosphate also improve the shortcomings of dehydrated ethyleneamine polyphosphate with respect to moisture sensitivity and handling. The primary unexpected findings are much higher thermal stability by drying conditions suitable for molecular weight enhancement for condensation polymers, elimination of phosphorous containing waste stream, and improved anti drip performance in a flame for polymers containing these flame retardant compositions.

DETAILED DESCRIPTION OF INVENTION

The synthesis of flame retardants using polyphosphoric acid are disclosed in U.S. Pat. No. 7,138,443, U.S. application Ser. No. 10/497,129 and US patent application 20090048372. The entire disclosure is incorporated herein by reference.

Unless the context indicates otherwise, in the specifications and claims, the terms such as a flame retardant syrup, dehydrated ethyleneamine polyphosphate, flame retardant composition, filled flame retardant composition, flame retardant containing composition, filled flame retardant containing composition, ethyleneamine, polymer, and similar terms includes mixtures of such materials. Unless otherwise specified, all percentages are percentages by weight and all temperatures are in degrees Centigrade (° C.). All thermo graphic analysis (TGA) is performed in nitrogen at 20° C. per minute.

Ethyleneamines are defined here as ethylene diamine and polymeric forms of ethylene diamine including piperazine and its analogues. A thorough review of ethyleneamines can be found in the Encyclopedia of Chemical Technology, Vol 8, pgs. 74 108. Ethyleneamines encompass a wide range of multifunctional, multireactive compounds. The molecular structure can be linear, branched, cyclic, or combinations of these. Examples of commercial ethyleneamines are ethylenediamine (EDA), diethylenetriamine (DETA), piperazine (PIP), triethylenetetramine (TETA), tetraethylenepentamine (TEPA), and pentaethylenehexamine (PEHA). Other ethyleneamine compounds which are part of the general term ethyleneamine polyphosphate which may be applicable are, aminoethylenepiperazine, 1,2-propylenediamine, 1,3-diaminopropane, iminobispropylamine, N-(2-aminoethyl)-1,3-propylenediamine, N,N'-bis-(3-aminopropyl)-ethylenediamine, dimethylaminopropylamine, and triethylenediamine. Etyleneamine polyphosphate can be formed with any of these ethyleneamines. The preferred is EDA and DETA. All examples use ethyleneamine polyphosphate made with DETA. Certain acids are expensive to obtain in very pure form. Pyrophosphoric and polyphosphoric acid can be contaminated with orthophosphoric acid unless freshly prepared as these two acids convert to orthophosphoric in aqueous medium, with the rate being dependent on many factors such as temperature and water content. Polyphosphoric acid can be prepared from the appropriate pure sodium salts using the acidic ion exchange resin: for example, strong acid cation exchange resin from Purolite Corp., Philadelphia, Pa. An aqueous solution of the appropriate salt (LC Vitrophos sodium polyphosphate from Innophos Corporation, Cranberry, N.J., average change length 19-21 units) is passed through an ion exchange column containing Purolite strong cation resins (Purolite Corp., Philadelphia, Pa.), at which time almost all the sodium ions are removed leaving the pure acid. The sodium polyphosphate according to Innophos Corporation contains about 15% low molecular weight content that is undesirable as it lowers the amount of long chain polyphosphoric acid. The acidity of the prepared acid will depend on whether all the sodium ions are removed. Thus not all the sodium must be removed to prepare the flame retardants of the invention. The most preferred is pH less than 1.0. Addition of ion exchange resin via a batch method does not remove all the sodium ions unless repeated a few time. It is preferred to use an ion exchange column to remove nearly all the sodium ions, but other methods are applicable.

The molar unit for pyrophosphoric acid is $H_4P_2O_7$. The molar unit for polyphosphoric acid is assumed to be $(HPO_3)_n$, in this work with the molecular weight assumed to be derived from $(HPO_3)$. With there being 3 or more units in a polymeric chain, the true molecular weight could be quite large as n molar units are involved with a terminal (OH) group. Such considerations are used to determine the correct reaction ratios. For all polyphosphoric acid calculations, the molecular weight will be based on the unit $(HPO_3)$ even though that is only an approximate molecular weight.

Polyphosphoric acid, a commercially available form, can also be prepared by heating $H_3PO_4$ with sufficient phosphoric anhydride to give the resulting product, an 82-85% $P_2O_5$ content, as described in the Merck Index 10.sup.th edition, #7453.

In U.S. Pat. No. 7,138,443 and US patent application 20090048372, the preferred process to make ethyleneamine polyphosphate consists of (1) dissolving sodium polyphosphate in water, (2) adding the sodium polyphosphate solution to an ion exchange column to form polyphosphoric acid, and then (3) reacting an ethyleneamine with the aqueous solution of polyphosphoric acid prepared by ion exchange. The most preferred ethyleneamine was DETA. In U.S. Pat. No. 7,138,443, the entire solution was dried in a vacuum oven to form DETA polyphosphate (DetaPP). The conditions for vacuum drying were not discussed nor appreciated. In U.S. Pat. No. 7,138,443, no syrup formation was reported. In US patent application 20090048372, the aqueous solution consisted of a viscous syrup that is collected and a non viscous solution that is discarded. The syrup is dried to form the product. In US patent application 20090048372, the yield is low and there is a significant non viscous phase containing phosphates. The non viscous phase was regarded as a waste stream whose disposal was not addressed. The ethyleneamine polyphosphate was reported to have a weight loss of about 1% at 300° C.

The syrup will be referred to as a flame retardant syrup. The syrup dried in a vacuum oven will be referred to as dehydrated ethyleneamine polyphosphate or a flame retardant composition. Filled flame retardant composition is dehydrated ethyleneamine polyphosphate filled with additives. Polymers containing the flame retardant composition will be referred to as a flame retardant containing composition. Polymers containing the filled flame retardant composition as well as additives will be referred to as filled flame retardant containing composition. Dehydrated ethyleneamine polyphosphate is used to designate ethyleneamine polyphosphate that has been processed to have a significantly higher molecular weight or cross linking which overcomes some of shortcomings of typically prepared ethyleneamine polyphosphate.

This invention is a flame retardant syrup prepared by a method comprising the steps of (a) dissolving sodium polyphosphate in the non viscous phase of previous run for making ethyeleneamine polyphosphate or dehydrated ethyleneamine polyphosphate via ion exchange, (b) adding such sodium polyphosphate solution to IX column to obtain a modified polyphosphoric acid (c) reacting an ethyleneamine or a mixture of ethyleneamines with the modified polyphosphoric acid, (d) collecting and separating syrup from dilute non viscous phase, with said non viscous phase saved for next iteration. The preferred ethyleneamine is DETA which yields a viscous syrup with a density of about 1.43 g/cm3 that precipitates in the reaction vessel. The non viscous phase has a density of about 1.03 g/cm3. The density of the non viscous phase is very sensitive to how much water is used to flush the ion exchange resin. The non viscous phase contains ethyleneamine polyphosphate product of lower thermal stability as compared to the syrup and it has not been economical to recover product from such a non viscous phase. So, it was very surprising that inclusion of the lower thermal stability non viscous phase would yield ethyleneamine polyphosphate of equivalent or better thermal stability. The best yield obtainable now is at lease 95% as compared to previous 85%. The pH of the viscous and non viscous phase is sensitive to the amount of ethyleneamine. We claim any ratio that produces syrup. The preferred pH range is from 1 to 7. The most preferred is from about 1.8 to about 5. Viscous phase is also referred to as syrup or flame retardant syrup.

In U.S. Pat. No. 7,138,443 and US patent application 20090048372 little is mentioned about the drying conditions. In U.S. Pat. No. 7,138,443 and US patent application 20090048372 a weight loss of 1% or so at 300° C. was reported and dried non viscous phase as weight loss near 10%. The claim is only that the weight loss be less than 1.5% at 315° C.

It is found that the drying conditions have a dramatic impact on the thermal stability and performance of the ethyleneamine polyphosphate.

In this work, it has been unexpectedly observed that drying ethylenenamine polyphosphate appears to be simply dehydrating and condensation. The following work used a syrup of diethylenetriamine polyphosphate as the test sample. The first stage was to remove the water from the syrup. In a tray dryer vacuum oven set at 190° C., the vacuum was powerful enough to reach mili Torr readings in less than one hour and was used here. Almost immediately upon installing the sample, one sees the syrup bubbling as the water was removed. The vacuum is at least 50 Torr during this stage as much water is being released. The bubbling slowly becomes a foam that rises well above the pan about 6 to 10 inches high, as if bubbles are being blown. After foaming stops, a clear yellowish liquid was observed in the pan. This can then be cooled and used in an extruder. This material has a weight loss of about 1% at 300° C., consistent with the claims in U.S. Pat. No. 7,138,443 and US patent application 20090048372 and is designated DetaPP. This behavior was observed for large samples dried at maximum vacuum of 50-100 Torr. This type of sample was described in U.S. Pat. No. 7,138,443 and US patent application 20090048372. As already mentioned, 50-100 Torr can yield a much more stable product if a small sample was dried.

The vacuum conditions for the above were repeated for an identical sample. The first stage of bubbling proceeded to foaming which proceeded to a clear viscous liquid. The advance made here was to recognize the impact of continuing to apply vacuum. As the strong vacuum continued to be applied, surprisingly the clear viscous liquid began to fluff as if nitrogen were blown through it. This fluffing was continued for two hour, then removed. The above sample DetaPP poured easily out of the pan. This sample had to be scrapped out of the pan. The new material still looks like a yellowish clear, brittle glass like solid when removed and cooled. It's TGA results are very different in that the weight loss at 345° C. now averages about 0.2% to 0.5%, an incredible improvement over the results of U.S. Pat. No. 7,138,443 and US patent application 20090048372. This new material was still soluble in water and it continued to behave like a polymer in that it melted into polymers in extrusion. This further dried DetaPP will be called DDetaPP to distinguish the extra drying time that results in a product with many advantages and is applicable to other ethyleneamines. Thus, DDetaPP was simply a much more dehydrated form of DetaPP, with the water a result of condensation as is well known for condensation polymers but surprisingly found in this system.

Thus, the very strong vacuum at high temperature appears to cause a condensation and or cross linking to occur as is known for sodium phosphates. The condensation can be between polyphosphate chains emitting water. There could also be condensation between ethyleneamines. No smell of ammonia is observed suggesting this is a lower probability event. Thus, drying under vacuum appears to cause condensation and cross linking which leads to more stable product. The more stable product is then effective in flame retarding polymers because the higher decomposition temperature is closer to that of polymers. The processing is better as less volatiles emitted. Long term aging due to moisture is better.

The DetaPP and DDetaPP cab be further distinguished by the measured melt flow rate at 160° C. The DetaPP is measured to have at least 20% higher melt flow rate than DDetaPP for a weight of 5 kg for 10 minutes. This sort of result, that DDetaPP is more viscous than DetaPP is found for polymers as a function of molecular weight and cross linking. This indication of increase in molecular weight/cross linking was further supported by TGA. A 20-45 mg irregularly shaped sample of DDetaPP does not melt to a nearly flat state when it is heated in a TGA to 345° C. at 20° C. per minute in nitrogen. The sample comes out of the TGA rounded, but still about the same height and is easily removed out of the TGA platinum pan. A similarly shaped sample of DetaPP melts into a flat state in the TGA pan heated under the same TGA program, as it completely melted since it has high melt flow. Low melt flow prevented DDetaPP from flowing, even above 300° C. These properties have been tested for pH 1.8 to 4.5.

It is further interesting to dissolve DDetaPP in water at a rate of 3 g per 20 g water in a graduated cylinder. It is found that about 3 ml of syrup are formed at the bottom and a clear interface is formed. A similar experiment performed with DetaPP yields at least 15% less syrup and the interface is a little fuzzy and about 0.25 inches or more wide. Sometimes practically little or no syrup is found when DetaPP is dissolved in water. This further supports our theory that DDetaPP has the properties of higher molecular weight and that the fluffing in the drying cycle is causing such effect.

The use of non viscous phase results in higher yield (more syrup) and less waste product, which was unexpected. We had expected that the concentration of polyphosphates in the non viscous phase would increase and the amount of non viscous phase would increase, which did not occur. The non viscous phase is thought to be of lower molecular weight. A reasonable explanation is that the lower molecular weight of the non viscous phase has been taken care of by the vacuum drying, done at conditions that increase the molecular weight of condensation polymers such as polyester (PET).

The process for making DDetaPP is at least 15% more efficient. One interpretation, the sites that water had been attached to are now bonded to a low molecular weight DETA polyphosphate from the non viscous phase which results in extending the chain length or cross linking the polymeric chains. We have chosen conditions used to increase the viscosity of polyethylene terephthalate (PET) and have used as a model for increasing thermal stability of ethyleneamine polyphosphate. Novel drying techniques for PET such as hot nitrogen should be applicable here.

DDetaPP is more stable and has decomposition temperatures closer to that of polymers. Thus, DDetaPP is a better flame retardant than the standard ethyleneamine polyphosphate. The only distinguishing characteristic between them appears to be molecular weight and or cross linking.

Our interpretation of the chemistry and TGA results is qualitative and does not bind the invention which rests on its own properties. Thus, it appears that DDetaPP is a dehydrated DetaPP, and thus the name dehydrated ethyleneamine polyphosphate. It appears that the new process has reduced the sites at which a species such as water are attracted. Thus, an extremely stable flame retardant composition results which is inherently different and a higher molecular weight form of ethyleneamine polyphosphate. Thus, this new form of ethyleneamine polyphosphate can be extruded at very high temperatures without release of volatiles that could make extrusion difficult. To obtain this form of ethyleneamine polyphosphate it is necessary to use a vacuum dryer that achieves a vacuum of at least 25 Torr and the temperature should be between 150° C. and 220° C. The preferred is a final vacuum reading of 10 Torr or less and the most preferred is final vacuum of 5 Torr or less. The preferred temperature range is 170° C. to 200° C. The most preferred temperature is 190° C. to 200° C. These results were accomplished with a tray dryer. A rotary dryer should also work as well. The time used in our results was in the range of 2 to 5 hours. A time range is difficult to establish as the amount of syrup being dried and the depth in pans greatly effects how quickly drying takes place. The important factor is to use temperature, time, and vacuum that goes beyond the foaming to clear liquid and then to fluffing. As the fluffing continues, the vacuum will approach 1-5 Torr, at which time we normally remove the sample. The improvement with further time appears to be small and not worth the cost as it takes a long time to obtain mili Torr. Small samples can dry with poorer vacuum.

The thermal stability above 350° C. can vary with pH. For pH between 1.8 and 4.1, the weight loss in TGA at 20 C per minute has been less than 0.6% at 345° C. A very small sample (20 g) of syrup dried at 100 Torr had a weight loss of 0.4% at 345° C. The above considerations of vacuum are intended for large samples where a strong vacuum would obtain very stable product in a reasonable time frame.

The non viscous phase with a density of 1.03 g/cm**3 was thoroughly dried in a vacuum oven. The TGA of the non viscous phase at 20° C. per minute in nitrogen has a weight loss of 0.54% at 150° C., 0.7% at 250° C., 0.9% at 300° C., and 1.4% at 345° C. A sample of syrup made with DETA and a pH of 2.1 has a weight loss of 0.25% at 345° C., which is far superior. A sample made with Soda Phos sodium polyphosphate (average chain length of 5-6 from Innophos has a weight loss of 0.6% at 345° C. Those samples had been dried simultaneously. Thus, the data would suggest that the non viscous phase contains the lowest molecular weight. A sample made with Soda Phos has molecular weight between that of the non viscous phase and that made with long chain sodium polyphosphate. It is thus surprising that incorporation of the non viscous phase does not lead to product with lower thermal stability. It would also seem reasonable to expect that the non viscous phase of low molecular weight product would increase as several iterations are run. The non viscous phase has a relatively stable density of about 1.03%, for constant amount of liquid used. The amount of syrup is sharply higher by at least 5-10%, as if the non viscous phase has been incorporated into the syrup. It had been expected that the thermal stability of such dried syrup would be lower and possibly unacceptably lower. The reduced waste product and higher yield make it a worthwhile alternative to DetaPP. Syrup and viscous phase are used interchangeably.

To understand the compositional differences of ethyleneamine polyphosphate and dehydrated ethyleneamine polyphosphate, the process differences need to be fully understood. The non viscous phase should move through the ion exchange resin pretty much unreacted. This new process starts with the non viscous phase containing lower molecular weight ethyleneamine polyphosphate reacting with polyphosphoric acid to form modified polyphosphoric acid, and before the ethyleneamine is added. Water should be most tightly bound to the highest acidity sites which are the ends of the polymeric acid chains. Then, the ethyleneamine is added to this partially reacted polyphosphoric acid/ethyleneamine polyphosphate to complete the reaction. The dehydrated ethyleneamine polyphosphate composition in being a two stage reaction forms a new composition dehydrated ethyleneamine polyphosphate fundamentally different from the ethyleneamine polyphosphate in U.S. Pat. No. 7,138,443 which is obvious from the TGA's, the increased melt viscosities, and reduced sensitivity to water. Ethyleneamines such as DETA have long been used to extend and cross link polymers. It is not a surprise that such extension and cross linking occurs here along with the elimination of acid sites that bonded water. Other ethyleneamines might be even more effective than DETA.

There are other ways to accomplish this synthesis. Obviously, an aqueous solution of ethyleneamine polyphosphate could accomplish the same task as the non viscous phase. Other chemicals such as urea or melamine might also do the same and appear to be different compositions although they have the same underlying chemistry.

Obviously, instead of using the non viscous phase, one could possibly substitute low molecular weight ethyleneamine polyphosphate or ethyleneamine phosphate dissolved in water for the non viscous phase and get a very similar product. Thus, there are other ways of modifying the polyphosphoric acid that would have the essentially the same result. Environmentally, use of the non viscous phase is the most desirable route. It is also probably not necessary to run the non viscous phase through the IX column and just add it to the collection tank. However, that would increase the amount of water used in the overall process significantly, an environmental negative. Such obvious changes to the process as well as others to many to include would be considered as part of this invention. There are other chemicals such as urea mixed with the sodium polyphosphate that might give the same result. The same composition of matter would result if the TGA were similar. We can only define our new composition DDetaPP by its unique properties (such as TGA, very low melt flow, and synthesis ingredients) as crystal structures cannot be obtained. We have not embarked on such research as it is environmentally desirable to have a process which incorporates the non viscous phase. We do generate sodium chloride in regenerating the IX column, but that will be extracted and sold as animal feed and road salt since the purity is very high. Sodium chloride solutions are normally accepted by publicly owned treatment facilities (POT).

Many flame retardants are new compositions of matter defined by new processes with new properties. Ammonium polyphosphate is completely soluble in water. However, a flame retardant is sold as APP (ammonium polyphosphate) and it has very low solubility in water. APP is a different composition of matter than ammonium polyphosphate as it is made under pressure with urea at high temperatures to obtain the low solubility in water. Technically, APP is not ammonium polyphosphate as it contains urea in some undefined way as crystal structures are not available. A similar situation occurs for melamine polyphosphate. A flame retardant is sold as melamine polyphosphate or commercially supplied as Melapur 200. However, technically, it is melamine phosphate heated with a specific temperature profile to yield a product that is much more thermally stable than if one had directly reacted melamine and polyphosphoric acid.

This invention is also filled flame retardant composition comprising ethyleneamine polyphosphate which further contains fillers selected from the group of organic phosphates; melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates. The fillers with the exception of organic phosphates can be added to the syrup before drying with the risk of some reaction during prolonged drying. The fillers can be added to the ethyleneamine polyphosphate in the melt after drying or by re-melting and adding. All of these additives appear to work. The preferred is Aerosil R972 and BDP. The more preferred is a loading of about 1-5%. The most preferred is about 1-3%. Flame retardants like hydrophobic Aerosil R972 separate partially and become unevenly distributed if mixed into the syrup and then dried. Melamine containing fillers can be added over a much wider range depending on the application. The preferred is about 0.5% to 15%. Thus, the preferred is to add the fillers to the ethyleneamine polyphosphate after drying. This could be done in a rotary vacuum dryer as the last stage after drying just before extraction. An extruder or mixer such as a Banbary could also be used.

This invention is also a flame retardant containing composition comprising: a) 30 to 99.75 percent by weight of a polymer; and b) 0.25 to 70 percent by weight of the flame retardant composition selected from dehydrated ethyleneamine polyphosphate and filled dehydrated ethyleneamine polyphosphate. The loading depends on the application.

This invention is also a filled flame retardant containing composition comprising: a) 30 to 99.75 percent by weight of a polymer; b) 0.25 to 70 percent by weight of flame retardant composition selected from group of dehydrated ethyleneamine polyphosphate and filler filled dehydrated ethyleneamine polyphosphate and c) 0.01 to 40% of one or more compounds selected from group of organic phosphates; melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates. The preferred is dehydrated Deta ethyleneamine polyphosphate (DDetaPP) with 1-4% loading of Aerosil R972. EDA polyphosphate works as well as DETA ethyleneamine polyphosphate but requires more extensive equipment to work with. The addition of fumed silica filler is the most preferred as it is the most effective method to stop sagging of sample that occurs in UL94 test. Organic phosphates such as BDP are added at levels of 1% to 10% to enable compatibility.

Fumed metal oxides are becoming available with different metals. Currently widely available are fumed silica, fumed aluminum oxide, and fumed titanium oxide. Experimental nanostructures have been reported by Degussa such as indium tin oxide (ITO), zinc oxide, ceria, and various composites. The preferred here is fumed silica. Even more preferred is fumed silica surface treated to be hydrophobic. The most preferred is surface treated with dimethyldichlorosilane (DDS), silicone oil, or BDP.

Polymers can be flame retarded with dehydrated ethyleneamine polyphosphate, filled dehydrated ethyleneamine polyphosphate and fillers. The preferred ethyleneamine is DDetaPP and the preferred filler is hydrophobic fumed silica in order to improve flame retardant behavior. It is possible to add in an extruder with feeders directly polymer, dehydrated ethyleneamine polyphosphate, and fumed silica. More preferred is to mix the fumed silica and dehydrated ethyleneamine polyphosphate together in a heated mixer such as the rotary vacuum dryer, a Brabender, a Banbary, or an extruder and then add to a polymer in the appropriate mixer, with more fumed silica if necessary.

For example in a Brabender, add about 2.5 g fumed silica treated with DDS (Aerosil R972 from Degussa corp.) and then add 55 to 62 g of DDetaPP. DDetaPP containing fumed silica is referred to as DDetaPP-FS.

The flame retardants can be added to synthetic polymers, both thermoplastic and thermoset as well as polymeric coatings, epoxies, and paints. The field of applicability is not limited.

The flame retardant syrup could be sprayed onto trees or plants in the path of a forest fire to protect the wood substrate. The syrup forms a protective char when a flame is applied and greatly reduces the fuel content for moderate temperatures and prevents flaming or glowing embers. This effect works for any pH syrup. The syrup for this application is referred to as a protective barrier composition.

Flame retardant containing polymer compositions can be prepared conventionally in a melt mixer such as a Brabender mixer, a Banbary mixer, a single screw extruder, a twin screw extruder, or any other such devise that melts polymer and allows addition of fillers and through mixing. A Brabender, Buss Kneader or Farrell mixer will be preferred for some polymers and an extruder for other polymers.

The flame retardant containing polymer composition may contain other additives such as other flame retardants, standard carbon forming compounds, and re-enforcing agents, a partial list being chopped glass, aramid fibers, talc, mica, nano-clay, or clay. Since flame retardants work by different mechanisms, a combination of our flame retardant with other flame retardants (but not ATH and magnesium hydroxide) may perform more efficiently. Other additives include such ingredients as stabilizers, release agents, flow agents, dispersants, plasticizers, and pigments.

The classes of polymers to which the flame retardants are applicable are not limited to the following but shall include all polymers. And in particular shall include the following: acrylic, butyl, cellulosics, epoxy, furan, melamine, neoprene, nitrile, nitrocellulose, phenolic, polyamide, polyester, polyether, polyolefin, polysulfide, polyurethane, polyvinyl butyral, silicone, styrene-butadiene, butyl rubber, and vinyl.

Polymer and polymer compositions to which the flame retardants of the invention are applicable to include the following: 1. Mono and diolefins such as polypropylene (PP), thermoplastic olefins (TPO), polyisobutylene, polymethylpentene, polyisoprene, polybutadiene, polyethylene with or without cross linking, highdensity polyethylene, low density polyethylene, or mixtures of these polymers. Copolymers of mono and diolefins including other vinyl monomers such as ethylene-propylene copolymers, ethylene-vinyl acetate copolymers. Terpolymers of ethylene with propylene and a diene such as hexadiene, cyclopentadiene or ethylidiene norborene and vinyl monomers such as vinyl acetate. Mixtures of polymers under 1. 2. Polystyrene, poly p methyl styrene, poly.alpha. methylstyrene, and copolymers of styrene or .alpha.methylstyrene with dienes or acryl derivatives such as styrene-butadiene, styrene-actrylonitrile, styrene-alkylmethylacrylate, styrene-butadiene-akylacrylate, styrene-maleic anhydride, and styrene-acrylonitrile-methylacrylate. 3. Polyphenylene oxide and polyphenylene sulfide and their mixtures with styrene polymers or with polyamides. 4. Polyurethanes derived from polyethers, polyesters and polybutadiene with terminal hydroxy groups on one hand and aliphatic or aromatic polyisocyanates on the other as well as their precursors. 5. Polyamides and copolymers derived from diamines and dicarboxylic acids and/or from aminocarboxylic acids or the corresponding lactams, such as polyamide 4, polyamide 6, polyamide 6/6, 6/10, 6/12, 4/6, 66/6, 6/66, polyamide 11, polyamide 12, aromatic polyamides based on aromatic diamine and adipic acid: and iso- and/or terephthalic acid and optionally an elastomer as modifier, for example poly-2,4-trimethyl hexamethylene terephthalamide, poly m phenylene-isophthalamide. 6. Polyesters derived from dicarboxylic acids and dialcohols and/or from hydrocarboxylic acids or the corresponding lactones such as polyethylene terephthalate, polybutylene terephthalate, polyethylene terephthalate/polybutylene terephthalate mixtures, polyethylene terephthalate/polybutylene terephthalate copolymers, poyl 1,4-dimethyl ciclohexane terephthalate, polyhydroxybenzoates, and co-polymers with ethylene. 7. Polyvinyl chloride and copolymers with ethylene, copolymers of tetra fluro ethylene and ethylene. 8. Thermoset polymers include for example unsaturated polyester resins, saturated polyesters, alkyd resins, amino resins, phenol resins, epoxy resins, diallyl phthalate resins, as well as polyacrylates and polyethers containing one or more of these polymers and a cross linking agent. A review of thermosets is found in Ullmann's Encyclopedia of Industrial Chemistry, Vol A26, p 665 9. Polymers for insulation such as fluorinated ethylene-propylene (FEP), cross linked polyethylene (XLPE), ethylene-propylene rubber (EPR), tree cross linked polyethylene (TRXLPE), and ethylene vinyl acetate (EVA). 10. Cellulose acetate, flexible polyurethane, rigid polyurethane. 11. Fluoropolymers and co-polymers such as TEFZEL®, DuPont Co, Wilmington, Del. Elastomers such as spandex as defined in Encyclopedia of Chemical Technology. Polyimides such as KAPTON®, DuPont Co., Wilmington, Del. And defined in Encyclopedia of Chemical Technology. 12. Polyethylene and its co-polymers. 13. Ethylene vinyl acetate, ethylene vinyl acetate carbon monoxide and ethylene n butyl acrylate carbon monoxide and ethylene n butyl acrylate glycidyl methacrylate, ethylene methyl, ethyl, and butyl acrylate ethylene (methyl, ethyl, buthyl) acrylate-vinyltrimethylsilane, or vinyltriethylsilane ethylene methyl acrylate and ethylene methyl acrylate MAME, ethylene acrylic and methacrylic acid, ethylene acrylic and methacrylic acid ionomers (Zn, Na, Li, Mg), maleic anhydride grafted polymers.

Aerosil R972 is post treated with DDS (dimethyl dichlorosilane). Aerosil R972 and Aerosil 200 are fumed silicas. Aerosil 8972 has a BET surface area of about 100 m2/g. The primary particle size is about 16 nm and the surface is hydrophobic. Aerosil 200 also has a BET surface area of about 100 m2/g. The primary particle size is about 16 nm and the surface is hydrophilic. The primary particle of Sil Co Sil 63 is a milled silica (US Silica, W. Virginia) with a particle size of 40 microns on average. Clearly, Sil Co Sil 63 does not significantly decrease surface sensitivity as does the fumed silicas but has much value as an inexpensive filler to be used with dehydrated ethyleneamine polyphosphate.

Some of the Aerosil products available from Degussa are formed from colloidal silica and are considered part of the invention.

There exists a new line of amorphous silica with particle of about 150 nm, referred to as Sidistar®. They are much less expensive than fumed silica. They appear to be less effective as drip suppressants but have other attributes as modulus enhancement.

Organic phosphates tend to be hydrophobic. Examples of organic phosphates are selected from the group consisting of resorcinol diphenyl phosphate (RDP), tris(butyl phenyl) phosphate, resorcinol bis-diphenylphosphate, bis-phenol A bis-diphenylphosphate, triphenyl phosphate, tris(isopropyl phenyl) phosphate, tri butyl phosphate, isopropyl triphenylphosphate, triarylphosphate, phosphate ester mixtures used as placticizers, and bis-phenol A bis-diphenylphosphate. Bisphenol A bis-diphenylphosphate commercially available from Akzo Nobel Chemicals Inc under the tradename of Fyroflex BDP has been found to mix well with DDetaPP. BDP is also available from Albemarle Corporation, Baton Rouge, La. as Ncendx P-30.

BDP is soluble in some solvents such as toluene and acetone, but insoluble in water. DDetaPP is soluble in water but not soluble in organic solvents. It was very surprising that Ncendx P-30 and DDetaPP could be mixed to together with heat in a Brabender. Thus, BDP can be used to compatibilize DDetaPP and some polymers and some additives such as fumed silica. For example, by wetting hydrophobic Aerosil R972 with BDP, better mechanical properties are obtained polymer for compositions containing DDetaPP and Aerosil R972. Better mechanical properties are obtained for DDetaPP containing polymeric compositions with or without Aerosil R972 when melamine pyrophosphate, melamine, or melamine polyphosphate are wetted by BDP. In practice, the fumed silica, BDP, and DDetaPP can all be blended together. The BDP eliminates tensile bars breaking at low elongation an especially big problem for compositions containing 40 wt % or more loading of flame retardants.

The BDP also helps achieve higher loading of DDetaPP into polymers. For a polymer such as ethylene vinyl acetate (EVA), a loading of about 30% of DDetaPP can be achieved. Addition of BDP to DDetaPP enables a higher loading. BDP has excellent compatibility with PC, ABS, PPO, and HIPS. Thus, addition of BDP to DDetaPP enables better compatibility between DDetaPP and these polymers. Thus, BDP is viewed as a compatibilizer between hydrophobic additives and polymers and hydroscopic DDetaPP. Other organic phosphates especially RDP should function similarly.

With proper mixing equipment, BDP and ethyleneamine polyphosphate can be mixed at all levels. At room temperature, BDP is a viscous liquid and DDetaPP is a solid. Addition of 25% BDP changes DDetaPP to a bendable solid. Higher loading should lead to a very viscous material. All loadings are claimed as addition of some DDetaPP to BDP will result in a more effective BDP since DDetaPP adds nitrogen and more phosphorous to BDP.

All treatments of fumed oxides are claimed in the patent. The treatments now disclosed are available as Aerosil products. There is DDS as in Aerosil R972. There is methylacrylic silane on fumed silica. There is octyl silane on fumed silica. There is octamethylcyclotetrasiloxane on fumed silica (Aerosil R106). There are grades of Aerosil surface treated with hexadecyl silane, octylsilane, methylacrylsilane, polydimethylsiloxane, hexamethyldisilazane (HMDS) (Aerosil R8200), silicone oil, silicone oil plus aminosilane, and HMDS plus aminosilane.

Coating fumed particles is well known by those practicing this art such as Degussa Corporation. A user relies on a company such as Degussa to furnish fumed oxides treated with these compounds. It would be impractical to develop such products independently.

Another way to improve the shortcomings of dehydrated ethyleneamine polyphosphate is to add both organo phosphates such as BDP and fumed oxide such as fumed silica. Examples are given demonstrating the improved properties. The preferred method with which to use BDP is to use with fumed silica. BDP alone dos not stop the sagging in UL94 test. The preferred is hydrophobic silica and BDP both added to dehydrated ethyleneamine polyphosphate. The particular properties desired will dictate whether BDP should be added to the formulation. BDP increases melt flow and may not be desirable for some situations. Moisture resistance and handling properties are improved by the addition of both fumed silica and BDP.

EXAMPLES

Comparative Example

Formation of DETA Polyphosphate, Method of US Patent Application 20090048372

Dissolve 50 pounds (222.5 moles) of long chain sodium polyphosphate (Innophos Corporation, Trenton, N.J.) in about 28 gallons of water. An ion exchange column containing about 52 gallons of strong acid ion exchange resin (Purolite Corporation, Philadelphia, Pa.) was prepared in the hydrogen form. The sodium polyphosphate solution was then passed thru the column and polyphosphoric acid was formed as sodium ions are removed. Collection of acid was begun once the outgoing solution reached a pH of 4. About 45 gallons of dilute polyphosphoric acid was collected. We then added about 6170 g (56 moles) of DETA to the polyphosphoric acid and the solution reached a pH 4. A syrup of density of about 1.43 g/cm3 precipitates at the bottom and the remaining solution has a density of only about 1.03 g/cm3. The amount of syrup collected was about 5.5 gallons, leaving about 40 gallons of non viscous phase. The syrup was dried in a vacuum oven at 200° C. Product removed after the foaming stops had a weight loss of about 1% at 300° C. Product that is allowed to go through fluffing stage in vacuum oven has a weight loss of 0.4% at 345° C. The product with a density of about 1.73 g/cm**3 was then ready for use in flame retarding polymers. The amount of product gave a yield of only about 81%. The non viscous phase of about 39-40 gallons is usually discarded, because it contains product of much lower thermal stability.

Example

Formation of Modified DETA Polyphosphate (DDetaPP)

Hydrochloric acid at 6% concentration was passed through the IX column to remove all sodium ions from the previous run. Adequate water was used to flush remaining hydrochloric acid from the column. Fifty pounds of long chain sodium polyphosphate (222.5 moles) was dissolved in about 28 gallons of the dilute non viscous phase of previous run. The sodium polyphosphate solution is then passed thru the IX column and polyphosphoric acid (reacted with the non viscous phase) is formed as sodium ions are removed. Collection of acid was begun once the outgoing solution reached a pH of 4. The remaining 17 gallons of dilute non viscous phase from previous run and 13 gallons of fresh water was subsequently passed through the column to remove remaining polyphosphoric acid and non viscous phase. About 45 gallons of acid solution was collected. We then added about 7551 g of DETA (73.3 moles) to the modified polyphosphoric acid pre-reacted with ethyleneamine polyphosphate and a solution of about pH 4 resulted. A syrup of density of about 1.43 g/cm3 precipitates at the bottom and the remaining solution has a density of only about 1.03 g/cm3. The amount of syrup collected was about 7.5 gallons, leaving about 38 gallons of non viscous phase. Some of the syrup was dried in a vacuum oven at 200° C. and full vacuum for about 2 hours. The vacuum pump has the capability to reach mili torr values. The preferred vacuum is one that reaches a vacuum of 5 Torr or less. The amount of product (DDetaPP) gave a yield better than 95%, with the non viscous phase reused for the next run and not part of waste stream. The modified DETA polyphosphate (DDetaPP) has a weight loss of 0.2% at 345° C. and nearly no weight loss at 300° C. A. small irregular shaped 21 mg sample maintained 75% of its heights in the TGA. The DDetaPP was also much more viscous than the regular DetaPP suggesting higher molecular weight or cross linking. The lower pH syrups result in the most stable TGA behavior. When 3 g were dissolved in 20 ml water, 3 ml syrup formed with a clear interface with the non viscous phase. This synthesis was repeated for pH 0.8 and 4.5. The results are nearly identical in that the weight loss at 345° C. is less than 0.3% and the irregularly shaped piece looses less than 33% of its height. Dissolving 3 g in 20 ml water gave at least 2 ml syrup.

The above procedure to prepare DDetaPP was repeated six times always reusing the non viscous phase. The density of the non viscous phase solution remained about 1.03 g/cm**3 and did not accumulate to become more dense.

The non viscous phase was also dried in the vacuum oven along side the syrup. It's TGA is distinctly different in that is has a weight loss of 0.55% at 150° C., 0.7% at 250° C., 1.38% at 345° C. Thus, it is really unexpected that inclusion of the dilute non viscous phase leads to higher yield, higher thermal stability, and incorporation of troublesome non viscous phase. Innophos Corporation has indicated that long chain sodium polyphosphate (average chain length 19-20) contains 5% chain lengths 1-3, 16% chain lengths 4-6, and 7% chain lengths 7-9 and the remainder long chain. The standard sodium polyphosphate(average chain length 6) contains 8% chain length 1-3, 26% chain length 4-6, and 7% chain length 7-9 and the remainder long chain.

Example FR syrup: A thin coating of flame retardant syrup was placed unto a standard ⅜ inch wooden dowel from Home Depot store. A propane torch was applied to the coated dowel. The stick chars but does not burn through even after five minutes. The coating greatly has reduced the fuel content. A similar test on an uncoated dowel results in complete burning and formation of burning embers. Thus, the syrup could be used to form a protective coating as in a forest fire or conventional fire to stop the spread of the fire. A stick sprayed with this syrup will not burn to form embers, the primary way a forest fire propagates.

In the following examples, the samples were mixed in a Brabender with a capacity of 60 cc. The temperature was set in the range of 175° C. for EVA to 205° C. for TPU. The rotational speed was 60 RPM. The mixed polymer was pressed into 125 mil plaques and then cut into ½ inch wide by 6-inch long strips at 125 mil thickness for UL94 testing. TPU was Estane 58315 Nat 035. The Ativa EVA (AT Plastics, Inc) had a vinyl acetate content of 18%.

Example DDetaPP. A 70 gram sample was prepared consisting of 48.5 gram TPU, 21.1 g DDetaPP, 1.7 g AEROSIL R972. The samples were V0 rating.

Comparative Example 1

A 55 gram sample was prepared in the Brabender consisting of 38 gram EVA Ateva, 17 g DetaPP. The sample failed V0 rating at 125 mills.

Comparative example 1 demonstrates the importance of adding the filler to stop sagging with temperature in UL94 test.

Examples showing that fumed silica enables V0 rating in UL94 test at 125 mills.

Ex. 1: A 70 gram sample was prepared consisting of 48.5 gram TPU, 21.1 g DDetaPP, 1.7 g AEROSIL R972. The samples were V0 rating.

EX 1a: A 70 gram sample was prepared consisting of 48.5 gram TPU, 21.1 g DDetaPP, 1.7 g Sidistar®, an amorphous silica of particle size about 150 nm. The samples were V0 rating.

Ex 2: A 70-gram sample was prepared consisting of 41.4 gram TPU, 20.7 g DDetaPP, 1.7 g Aerosil R972 and 6.2 g Melapur 200 (from Ciba Specialty Chemicals now part of BASF). The samples were V0 rating.

Ex. 3: A 55 gram sample was prepared consisting of 38 gram EVA Ateva, 16.3 g DDetaPP, 1.3 g Aerosil R972. The samples were V0 rating. A similar sample was prepared with DetaPP. Pressed plaques were placed in a basement in West Chester, Pa. for two weeks. The basement had a humidity of about 60-75%, as evidenced by water condensing on copper pipes. The sample made with DetaPP had a residue on the surface. The sample with DdetaPP did not have residue, showing the superior moisture resistance of DdetaPP because of its superior aging properties. The superior properties are attributed to higher molecular weight/cross linking.

Ex 4: A 55 gram sample was prepared consisting of 32.6 gram EVA Ateva, 16.3 g DDetaPP, 1.3 g Aerosil R972 and 4.9 g Melapur 200. The samples were V0 rating.

Example A: Set Brabender at 175 C and 60 RPM. One g of Areosil R972 was added to the Brabender. Then add 62.5 g of DDetaPP. Then add 1.5 g of Aerosil R972. The final product becomes a brittle material. The product was then crushed. This product was called DDetaPP-FS as it was the more preferred and used in examples.

Example B: Set Brabender at 175 C and 60 RPM. Add 2.5 g of Sil Co Sil 63 ground silica from US Silica to the Brabender. Then add 62.5 g of DDetaPP. The final product becomes a brittle material. The product was then crushed.

Example C: Set Brabender at 175 C and 60 RPM. One g of Areosil 200 was added to the Brabender. Then add 62.5 g of DDetaPP. Then add 1.5 g of Aerosil 200. The final product becomes a brittle material. The product was then crushed.

Example D: Add 2.5 g of Aerosil R972 to the Brabender and then add 62.5 g of DDetaPP.

Ex 5: Add 38 g of TPU to Brabender, then add 17 g Ex A. The result was V0.

Ex 6: Add 38 g of TPU to Brabender, then add 17 g Ex B. The result was V1.

Ex 7: Add 38 g of TPU to Brabender, then add 17 g Ex C. The result was barely V0.

Ex 8: Add 38 g of TPU to Brabender, then add 17 g Ex D. The result was V0.

Ex 9: Add 38 g of EVA Ateva to Brabender, then add 17 g Ex A. The result was V0.

Ex 10: Add 38 g of EVA Ateva to Brabender, then add 17 g Ex B. The result was V1.

Ex 11: Add 38 g of EVA Ateva to Brabender, then add 17 g Ex C. The result was barely V0.

Ex 12: Add 38 g of EVA Ateva to Brabender, then add 17 g Ex D. The result was V0.

Ex. 14: Add 34.5 g Starex ABS SD0170W to the Brabender set at 240 C. Then add 15.5 g DDetaPP-FS. Form a plaque of 125-mil thickness. The bars produced from this plaque pass UL94 V0.

Ex. 15: Add 34.5 g Starex ABS SD0150W to the Brabender set at 240 C. Then add 15.5 g DDetaPP-FS. Form a plaque of 125-mil thickness. The bars produced from this plaque pass UL94 V0.

Ex. 16: Add 48.4 g TPU to Brabender. Then add 20 g DDetaPP and 1.6 g Aerosil R972. The composition passes UL94 v0.

Ex. 17: Add 37.95 g PP to Brabender. Then add 17.05 g DDetaPP-FS. The composition passes UL94 V0 at 125 mil.

Ex 18: Add 28.5 g PP to Brabender. Then add 9.5 g Katon 1650. Then add 17 g DDetaPP-FS. The resultant polymer passes UL94 V0 at 125-mil thickness.

Ex 19: Add 27.5 g Ateva EVA to Brabender. Then add 11 g Silco sil 63. Then add 16.5 g DDetaPP-FS. The resultant polymer passes UL94 V0 at 125-mil thickness Ex 20: Add 27.5 g Ateva EVA to Brabender. Then add 13.75 g Silco sil 63. Then add 13.75 g DDetaPP-FS. The resultant polymer passes UL94 V1 at 125-mil thickness Ex 21: Add 24.75 g Ateva EVA to Brabender. Then add 13.75 g Silco sil 63. Then add 16.5 g DDetaPP-FS. The resultant polymer passes UL94 V0 at 125-mil thickness Ex 22: Add 24.75 g Ateva EVA to Brabender. Then add 16.5 g Silco sil 63. Then add 13.75 g DDetaPP-FS. The resultant polymer passes UL94 V1 at 125-mil thickness.

The examples 19-22 show that the replacement of polymer with sil co sil 63 does not reduce the amount of DDetaPP-FS needed for V0 rating.

Ex. 23: Add 41 g TPU to Brabender. Add 20.5 g DDetaPP. Add 8.2 g Mistron Vapor RE. Then add 0.2 g polymist F5A. The sample passes UL94 V0 at 125 mil thickness.

Ex. 24: Add 58.5 g DDetaPP to Brabender followed by 6.5 g BDP. The resultant product does not stick to the beaters of Brabender and was easily removed, showing the improved handling of DDetaPP by addition of the hydrophobic BDP.

Ex. 25: Add 37.95 g Ateva EVA to Brabender. Then add 17.05 g of Example 23. The composition does not pass UL94 V0 at 125 mil.

Ex. 26: Add 58.5 g DDetaPP to Brabender followed by 6.5 g BDP and 2.5 g Aerosil R752. The resultant product does not stick to the beaters of Brabender and was easily removed, showing the improved handling of DDetaPP by addition of both hydrophobic BDP and hydrophobic Aerosil R972.

Ex. 27: Add 37.95 g Ateva EVA to Brabender. Then add 17.05 g of Example 26. The composition does pass UL94 V0 at 125 mil. This flame retarded composition does not get sticky when placed in a 50% relative humidity environment for 1 month which improves another shortcoming of DDetaPP.

Ex. 28: Add 58.5 g DDetaPP to Brabender followed by 6.5 g BDP, 2.5 g Aerosil R752, and 6.5 g Mistron Vapor RE. The resultant product does not stick to the beaters of Brabender and was easily removed, showing the improved handling of DDetaPP by addition of both hydrophobic BDP, hydrophobic Aerosil 8972, and Mistron RE. The product is crushed into a coarse.

Ex. 29: Add 37.95 g Ateva EVA to Brabender. Then add 20 g of Example 28. The composition does pass UL94 V0 at 125 mil.

Ex Buss Kneader: Run Brabender to form 620 g of DDetaPP-FS. Using a Buss Kneader extruder, mix 620 g DDetaPP-FS and 1380 g Ateva EVA. The flame retarded Ateva was used to make samples at 125 mil thickness which passed UL94 V0 rating. The strand was not sticky coming out of the water batch. The pellitizer did not get gummed up with fines. The extruder when opened was easy to clean as the DDetaPP-FS did not stick to the mixing elements in the Buss Kneader. Wire 24 gauge coated with this polymeric composition at a thickness of 18 to 30 mil passed wire and cable test VW1. Cable jacket made from this composition over 4 pairs of Teflon coated wire of communication cable core also passed VW1 test. Thus DDetaPP-FS did not seem to have any of the six shortcomings outlined in the introduction.

Ex 30: Add 30 g Ateva EVA to Brabender. Then add 10 g melapur 200. Then add 20 g DDetaPP. The resultant polymer passe9 UL94 V0 at 125-mil thickness but the elongation was only 50%.

Ex 31: First, thoroughly mix together 10 g Melapur 200 with 2 g BDP and 0.3 g fumed silica Aerosil 200. Add this with 30 g Ateva EVA to Brabender. The resultant polymer passed UL94 V0 at 125-mil thickness but the elongation was now 300%. Such examples showed the compatibilizing of BDP.

I claim:

1. A method for preparing a flame retardant syrup comprising the steps of (a) dissolving sodium polyphosphate in non-viscous phase of previous run, (b) purifying such sodium polyphosphate solution via ion exchange resin to obtain a modified polyphosphoric acid, (c) reacting an ethyleneamine or a mixture of ethyleneamines with the modified polyphosphoric acid to form a two phase mixture, (d) collecting and separating flame retardant syrup from dilute non-viscous phase, with said non-viscous phase saved for next iteration.

2. The method of claim 1 in which the flame retardant syrup has a pH between 1 and 7.

3. The method of claim 1 or 2, in which the ethyleneamine or a mixture of ethyleneamines is selected from the group consisting of ethylenediamine, diethylenetriamine, piperazine, triethylenetetramine, tetraethylenepentamine, pentaethylenehexamine, aminoethylpiperazine, and mixtures thereof.

4. The method of claim 1 in which the flame retardant syrup further contain fillers selected from the group consisting of melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates.

5. The method of claim 1 additionally comprising after step d), e) dehydration of the flame retardant syrup to form ethyleneamine polyphosphate that exhibits a weight loss of less than 1% at 300.degree.C. as measured by TGA operated at 20.degree.C. per minute in nitrogen.

6. The method of claim 1 additionally comprising after step d), e) dehydration of the flame retardant syrup to form ethyleneamine polyphosphate that exhibits a weight loss of less than 1% at 345.degree.C. as measured by TGA operated at 20.degree.C. per minute in nitrogen.

7. The method of claim 1 additionally comprising after step d), e) dehydration of the flame retardant syrup to form ethyleneamine polyphosphate with the property that when 3 g are dissolved in 20 ml water, at least 1.5 ml of syrup forms with a clear interface with the non-viscous phase.

8. The method of claim 1 additionally comprising after step d), e) dehydration of the flame retardant syrup to form ethyleneamine polyphosphate with the properties: a) a weight loss of less than 1% at 345.degree.C. as measured by TGA operated at 20.degree.C. per minute in nitrogen, and (b) when 3 g are dissolved in 20 ml water, 2-3 g of syrup forms with a clear interface with the non-viscous phase.

9. The method of claim 5 with the ethyleneamine polyphosphate additionally containing, 0.01 to 40 parts per hundred parts by weight of the ethyleneamine polyphosphate, one or more compounds selected from the group consisting of organic phosphates; melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates.

10. The method of making a flame retardant containing composition by blending the ethyleneamine polyphosphate of claim 5 or 6 with a polymer.

11. The method of claim 10 with the flame retardant containing composition comprising a) 30 to 99.75 percent by weight of a polymer; and b) 0.25 to 70 percent by weight of the ethyleneamine polyphosphate of claim 5 or 6.

12. The method of claim 10 with the flame retardant containing composition additionally containing, 0.01 to 40 parts per hundred parts by weight of the flame retardant containing composition, one or more compounds selected from the group consisting of organic phosphates; melamine; melamine pyrophosphate; melamine polyphosphate; urea; fumed compounds; zeolite; fumed silica; amorphous silica; fumed titanium oxide; fumed mixed metal oxides; and fumed silica surface reacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates.

13. The method of claim 10 wherein the polymer is a thermoplastic.

14. The method of claim 13 wherein the thermoplastic is chosen from the group consisting of nylon, polyester, thermoplastic urethane, and olefin.

15. A method for forming a protective barrier composition by deposition of the flame retardant syrup prepared by the method of claim 1 onto a substrate or between two or of more substrates.

16. The method of making a flame retardant containing composition by blending the ethyleneamine polyphosphate of claim 7 with a polymer.

17. The method of making a flame retardant containing composition by blending the ethyleneamine polyphosphate of claim 8 with a polymer.

* * * * *